United States Patent [19]

Farabaugh

[11] 4,400,089

[45] Aug. 23, 1983

[54] METHOD OF AND APPARATUS FOR DETERMINING OPTICAL QUALITY OF AN ARTICLE

[75] Inventor: Aloysius W. Farabaugh, Verona, Pa.

[73] Assignee: PPG Industries, Inc., Pittsburgh, Pa.

[21] Appl. No.: 225,541

[22] Filed: Jan. 16, 1981

Related U.S. Application Data

[62] Division of Ser. No. 68,832, Aug. 1, 1979, Pat. No. 4,285,745.

[51] Int. Cl.³ .................. G01N 21/32; G01B 11/06
[52] U.S. Cl. .......................... 356/382; 65/29;
73/1 J; 73/159; 156/64; 156/99; 156/102;
156/106; 156/378; 356/376; 364/473; 364/563;
364/572; 364/825; 427/10

[58] Field of Search ............. 65/29; 73/15, 159;
156/64, 99, 102, 106, 378; 356/381, 382, 376;
364/473, 563, 572, 800, 825; 427/9, 10

[56] References Cited

U.S. PATENT DOCUMENTS

| 3,779,731 | 12/1973 | Pollock et al. ............. 364/473 X |
| 3,792,930 | 2/1974 | Obenreder ................. 356/209 |
| 3,799,679 | 3/1974 | Simko ..................... 356/200 |
| 3,808,077 | 4/1974 | Rieser et al. ............. 156/102 |

*Primary Examiner*—Robert A. Dawson
*Attorney, Agent, or Firm*—Donald C. Lepiane

[57] ABSTRACT

An interlayer material is scanned prior to laminating same with glass sheets to generate a thickness variation signal, a wedge angle signal and an optical power signal. The signals are then selectively filtered to determine the thickness variation, wedge angle and optical power of the interlayer after lamination.

14 Claims, 16 Drawing Figures

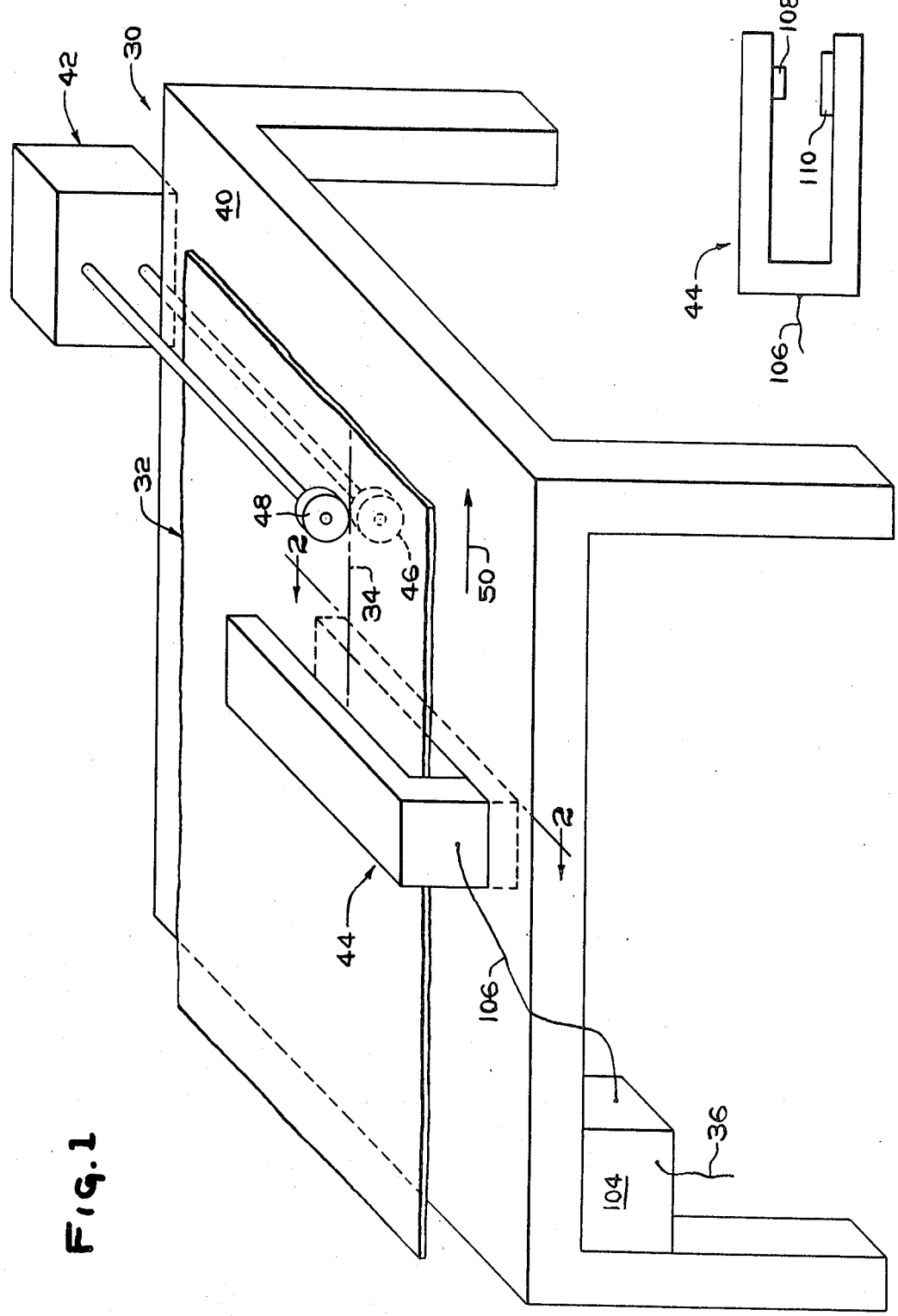
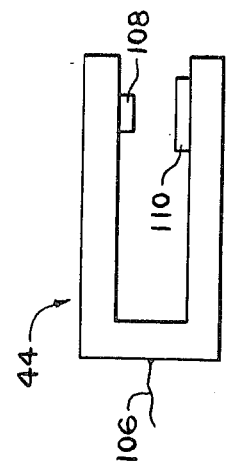
Fig.1
Fig.2

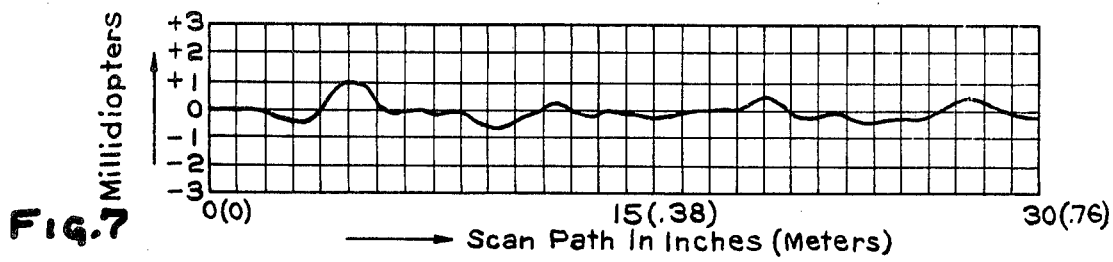
FIG.7
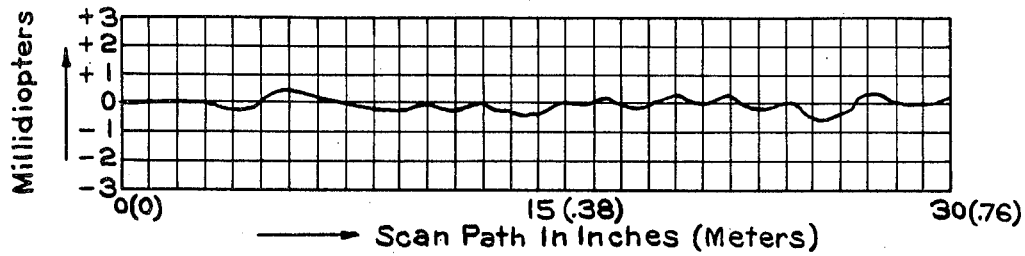
Fig.8
Fig.9
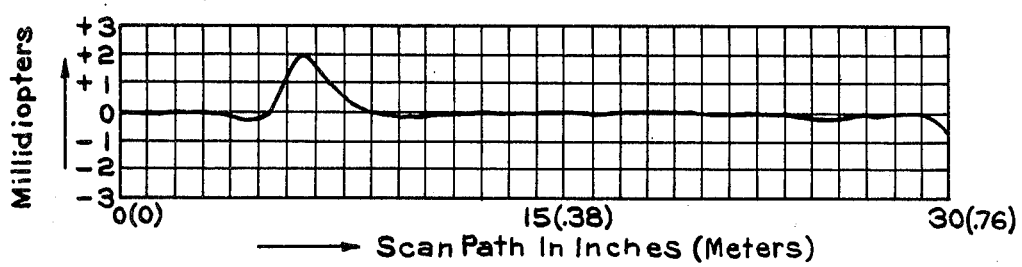
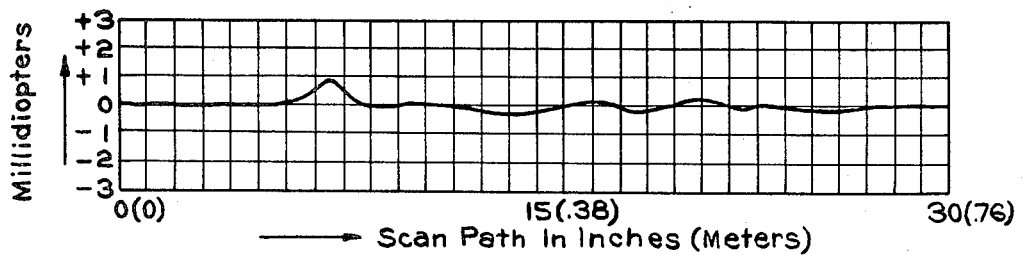
Fig.10

FIG.15 — Scan Path In Inches (Meters)

METHOD OF AND APPARATUS FOR DETERMINING OPTICAL QUALITY OF AN ARTICLE

This is a division of application Ser. No. 68,832, filed Aug. 1, 1979 now U.S. Pat. No. 4,285,745.

BACKGROUND OF THE INVENTION

1. Field of the Invention

This invention relates to a method of and apparatus for determining optical quality of an article.

2. Discussion of the Prior Art and Technical Problems

In the manufacture of laminated articles, e.g. automotive windshields it is desirable to know the quantitative value of the final optical performance of the laminate components prior to making the laminate. For example, to know or predict the optical performance of the interlayer material after lamination by inspecting the interlayer material prior to lamination. The prior art teaches that optical power value of glass plates are determined prior to lamination to determine if optically acceptable laminates can be made therefrom. More particularly, U.S. Pat. No. 3,639,112 teaches a distortion analyzer for scanning a glass ribbon and producing a trace proportional to the second derivative of glass thickness with respect to distance traversed. Windshield blanks are cut from sections of the glass ribbon where the second derivative has a minimal value. A limitation of the above technique is that it does not consider the optical contribution of the interlayer material which is laminated between the windshield blanks. The optical performance of the interlayer material should be known when it is realized that advances in glass technology have made it possible to produce glass ribbons that are substantially flat making the optical contribution of the interlayer material more predominant.

It would be advantageous therefore to provide a method of and apparatus for determining optical quality of an interlayer material prior to and after lamination by inspecting the interlayer material prior to lamination.

SUMMARY OF THE INVENTION

This invention relates to a method of determining profile of at least one property e.g. optical power of a worked article from the unworked article wherein the at least one property is altered during working of the article. The unworked article is scanned to generate a property profile of the unworked article afterwhich the profile is altered to determine the profile of the at least one property of the worked article.

This invention also relates to an improved method of making a transparent laminate including the steps of laminating at least one sheet to a plastic sheet. The improvement includes the steps of generating an optical profile of the plastic sheet prior to lamination and thereafter altering portions of the profile to determine optical contribution of the plastic sheet to the laminate.

Further, this invention relates to a method of controlling an article shaping process. An unshaped article is scanned to generate a property profile of the unshaped article. The property profile is altered to determine profile of the shaped article. After the article is shaped, a property profile of the shaped article is made and compared to the altered property profile of the unshaped article.

In addition, this invention relates to a method of determining at least one optical property of a plastic sheet by scanning the sheet to generate a thickness variation profile of the sheet along a scan path and thereafter acting on the thickness variation of the sheet to determine at least one optical property of the sheet.

Still further, this invention relates to an electrical system for determining at least one property of a worked article from the unworked article. The system includes facilities for scanning the unworked article to generate a profile of the characteristics of the at least one property of the unworked article operatively connected to altering facilities. The altering facilities alters portions of the profile to determine the characteristics of the at least one property in the worked article.

Also the invention relates to a method of calibrating the electrical system.

BRIEF DESCRIPTION OF THE DRAWING

FIG. 1 is an isometric view of an apparatus that may be used in the practice of the invention for inspecting interlayer material;

FIG. 2 is a side elevated view of the scanning head of the apparatus shown in FIG. 1;

FIG. 7 is a optical power signal of a glass sheet along a scan path across the draw (as defined in the Description of the Invention);

FIG. 8 is optical power signal of a second glass sheet along a scan path across the draw;

FIG. 9 is optical power signal of the sheet of FIG. 7 along a scan path with the draw (as defined in the Description of the Invention);

FIG. 10 is optical power signal of the sheet of FIG. 8 along a scan path with the draw;

DESCRIPTION OF THE INVENTION

Figure 3:
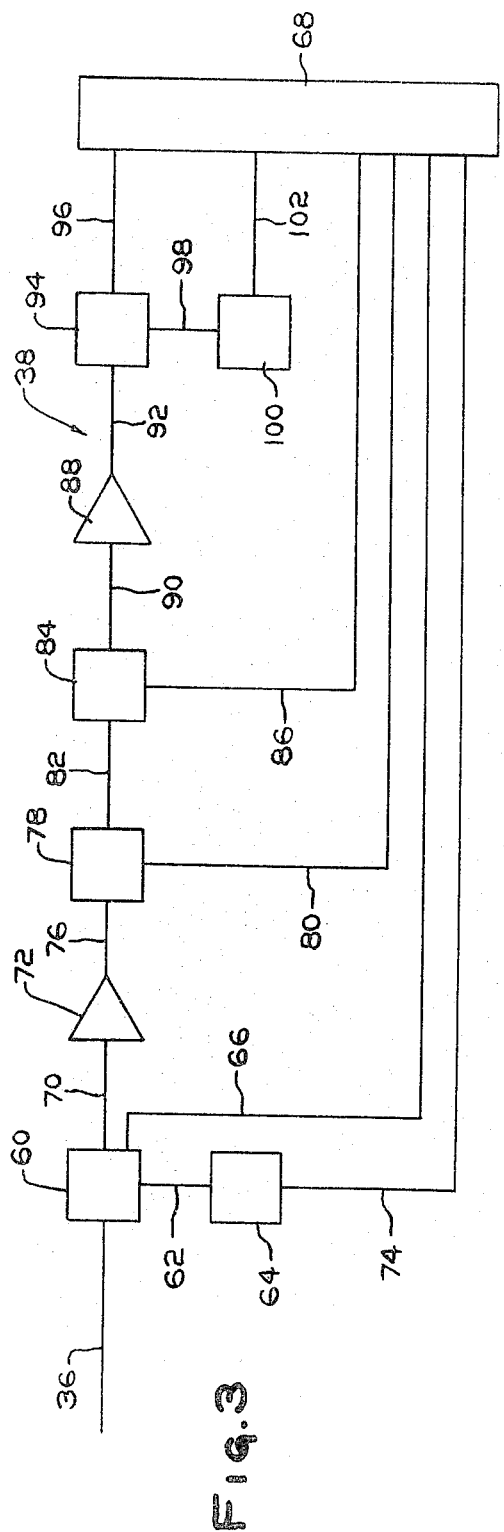
FIG. 3 is a block diagram of an electrical system that may be used in the practice of the invention for determining optical quality of interlayer material prior to and after lamination.

With reference to FIG. 1, there is shown an apparatus 30 for measuring thickness variation of sheet material 32 along scan path 34 and forwarding a signal which is a function of thickness variation along cable 36 to electrical system 38 shown in FIG. 3. The electrical system 38 in accordance with the teachings of the invention operates on the signal to determine mechanical and/or optical quality of the sheet material along the scan path and expected mechanical and/or optical quality of the sheet material in the final product. In the following discussion of the invention, the sheet material 32 is plasticized polyvinyl acetal sheet material of the type used in the manufacture of automotive laminated lites, for example, windshields of the type taught in U.S. Pat. No. 3,808,077, which teachings are hereby incorporated by reference. As will become apparent, the invention may be practiced for inspecting glass, plastics and/or synthetic resin materials.

The apparatus 30 includes a surface 40 for supporting the sheet material 32 and a drive arrangement 42 for metering the sheet material 32 through inspection head 44 to determine thickness variations of the sheet material 32 along the scan path 34. The drive arrangement 42 is not limiting to the invention and may include a bottom and upper wheel 46 and 48, respectively, for engaging and advancing the sheet material 32 therebetween in the direction of the arrow 50 at a predetermined speed through the inspection head 44. The inspection head 44 is not limiting to the invention and any convenient non-contacting or contacting sheet thickness measuring device may be used in the practice of the invention. Non-contacting measuring devices are preferred over contacting measuring devices because the interlayer material is soft and contacting same may give erroneous signals and/or damage, e.g., scratch the material. Non-contacting thickness measuring devices which may be used in the practice of the invention are capacitance thickness measuring devices or measuring devices of the type using an energy beam, e.g. a laser, X-rays or beta radiation in combination with a detector. In general, non-contacting thickness measuring devices using an energy beam and a detector operate on the principle of monitoring change in the beam as it passes through the material and/or is reflected from the sheet material. One type of non-contacting measuring device using energy beams is taught in U.S. Pat. Nos. 3,792,930 and 3,799,679, which teachings are hereby incorporated by reference. In the practice of the invention, it is recommended that the inspection head 44 be a capacitance thickness gauge because the shape of the capacitance detector is easily changed to correspond to expected lenses in the sheet material which is discussed in more detail below.

With reference to FIG. 3 the cable 36 is connected to a filter 60 to filter electrical noise from the signal. The signal from the filter 60 is forwarded (1) along cable 62 to filter 64; (2) along cable 66 to multi-channel recorder 68 and (3) along cable 70 to differentiator 72. The signal from the filter 60 to the recorder 68 along cable 66 is the thickness variation of the interlayer material along the scan path 34. The filter 64 filters out thickness variations in the interlayer material which are expected to be removed during the lamination process which is discussed in more detail below. The signal from the filter 64 forwarded along cable 74 to the recorder 68 is the expected thickness variation of the interlayer material in the laminated article.

The differentiator 72 differentiates the signal received from the filter 60 along the cable 70 and forwards the differentiated signal along cable 76 to filter 78. The differentiated signal from the differentiator 72 is a measure of wedge angle, i.e., parallelism of the surface or angle subtended by the tangents at the points of entry and emergence of a light ray passing through the material. The filter 78 filters out noise in the differentiated signal and forwards the filtered differentiated signal along cable 80 to the recorder 68 and along cable 82 to filter 84. That part of the signal which is filtered out is (1) extraneous signal pickup from the components of the electrical system; and (2) signal frequencies above a predetermined value which are of no interest in that they do not contribute to the wedge angle value in the laminated article and may result in saturation of the electrical components should the electrical components act on the signal. The signal forwarded along cable 80 to the recorder 68 is the wedge angle of the interlayer material along the scan path 34. The filter 84 filters out frequencies of the filtered wedge angle signal that are expected to be removed during the lamination process.

The signal from the filter 84 is forwarded along cable 86 to the recorder 68 and to differentiator 88 along cable 90. The signal forwarded along cable 86 to the recorder 68 is the expected wedge angle of the interlayer material in the laminated article or product. The differentiator 88 differentiates the signal received from the filter 84 along cable 90 and forwards the differentiated signal along cable 92 to the filter 94. The differentiated signal from the differentiator 88 is a measure of optical power. The filter 94 filters out noise in the differentiated signal and forwards the filtered differentiated signal along cable 96 to the recorder 68 and along cable 98 to the filter 100. The noise filtered out by the filter 94 is similar in nature to the noise filtered out by the filter 78 discussed above except that optical power values of no interest are filtered out by the filter 94. The signal forwarded along cable 96 to the recorder 68 is the optical power value of the interlayer material along the scan path 34. The filter 100 filters out frequencies of the optical power signals that are expected to be removed during the lamination process. The optical power signal from the filter 100 is forwarded along cable 102 to the recorder 68. The optical power signal from the filter 100 is the expected optical power contribution of the interlayer material to the laminated product.

Although not limiting to the invention, prior to inspecting the interlayer material, the electrical system 38 is calibrated in any convenient manner. The electrical system 38 may be calibrated with respect to optical characteristics, e.g., wedge angle and optical power by imposing a signal consisting of one frequency on the cable 36 which simulates thickness variations from which optical power can be calculated as shown in the following equations. In addition, the following equations mathematically show how optical power can be determined from thickness variations e.g. by using an electrical system.

$$T = C_1 A \text{ sine } \frac{2\pi f x}{s} + B \qquad (1)$$

where
T is the thickness of the material in inches (centimeters); for the calibrating signal T the thickness is set to a predetermined value;

$C_1$ is a conversion factor to convert the voltage signal from volts to inches e.g., 0.002 inch (0.0051 centimeters) per volt;

A is the amplitude of the thickness variation signal of the material in volts; for the calibration signal the amplitude A set is to a predetermined value;

f is the frequency in Hertz of the waveform reflecting thickness variation of the material; for the calibration signal the frequency f is set to a predetermined value that is below the cut off frequency of the lowest filter value of the electrical circuit;

x is the length of the scan path of interest in inches (centimeters);

s is the scan speed in inches (centimeters) per second and x/s is the scan time; and B is the nominal thickness of the material in inches (centimeters). The term B is constant and is shown in Equation 1 for completeness of the mathematical equation. In the calibration signal the term B is not used because it drops out when the signal passes through the differentiator 72. In the signal generated during the inspection of the material the Term B is normally accounted for by electronics 104 (see FIG. 1) associated with the inspection head 44.

The electronic system 38 is calibrated by imposing a sinusoidal thickness signal T having a predetermined amplitude $C_1 A$ on the cable 36 with the filters 60 and 64 set at their operating frequencies which are greater than the frequency of the calibrating signal. The signal received by the recorder 68 along cables 66 and 74 during the calibration should be the sinusoidal thickness signal imposed on the cable 36. If it is not, the recorder 68 and filters 60 and 64 are checked. If the signal is the same the amplitude $C_1 A$ of the calibration signal is measured on line 70. If the amplitude $C_1 A$ is not at a predetermined value for testing the differentiator, the voltage of A is changed until the signal measured on line 70 is at a predetermined value.

The first derivative of thickness with respect to the length of the scan path of interest (x) of Equation 1 is shown below in Equation 2 and is the wedge angle of the calibration signal of the material.

$$\text{arctangent } \frac{dT}{dx} = C_1 \frac{A2\pi f}{s} \text{ Cosine } \frac{2\pi f x}{s} \quad (2)$$

where

T, x, A, f, $C_1$ and s are as previously defined

The wedge angle in the electrical system is shown in Equation 3 below.

$$\frac{dT}{dx} = C_2 \frac{C_1 A 2\pi f}{s} \text{ Cosine } \frac{2\pi f x}{s} \quad (3)$$

where

T, x, $C_1$, A, f, and s are as previously defined;

$C_2$ is a conversion factor to convert volts to radians, e.g. 0.0029 radians per volt or to convert volts to minute of arc e.g. 10 minutes of arc per volt;

$C_1 A 2\pi f/s$ is the peak value of the wedge angle voltage signal; and dT/dx is in radians or minute of arc.

For small angles the angle in radians is approximately equal to the arctangent of the angle. Maximum wedge angle is calculated when Cos $2\pi f x/s$ is equal to 1 and appears on the recorder 68 as a peak value.

With the acceptable calibration signal imposed on calbe 36 the output signal from the differentiator 72 is tested at cable 76 or observed on recorder 68. If the tested or observed calibration signal is not equal to the value of dT/dx calculated for equation 3, the differentiator 72 is adjusted accordingly.

The first derivative of wedge angle (d/dx of Equation 2) times the index of refraction of the material minus one is the optical power of the material and is shown in equation 4.

$$OP = (n - 1)\frac{(2\pi f)}{s} \frac{(C_1 A 2\pi f)}{s} \frac{(-\sine 2\pi f x)}{s} \quad (4)$$

where $C_1$, f, x, A and s are as previously defined;

n is index of refraction of the material; and

OP is the optical power.

$C_1 A 2\pi f/s$ is radians $(2\pi f)/s$ is in units of 1/inches or 39.4 inches/meters The optical power as defined in the electrical system as shown in Equation 5.

$$OP = C_3(n-1)\frac{C_2 C_1 A 2\pi f}{s} \frac{2\pi f}{s}\left(-\sine \frac{2\pi f x}{s}\right) \quad (5)$$

where:

OP, n, $C_1$, $C_2$, A, f, x and s are as previously defined;

$C_3$ is a conversion factor to convert volts into diopters (radians per meter) e.g., 0.1 diopters per volt.

Maximum optical power is calculated where $(-\sine 2\pi f x)/s$ equals 1 and is observed as the peak value of the waveform.

With the calibrating signal imposed on cable 36 the output signal of the differentiator 88 is tested at cable 92 or observed on recorder 68. If the tested or observed calibration signal is not equal to the value of OP calculated for Equation 5, the differentiator 88 is adjusted accordingly.

Figure 5:
FIG. 5 is a view taken along lines 5—5 of FIG. 4.
Figure 6:
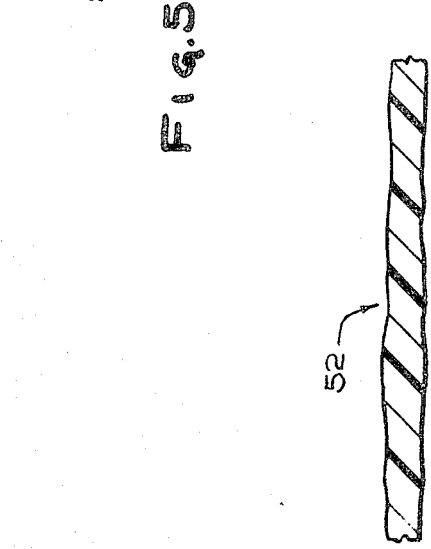
FIG. 6 is a view taken along lines 6—6 of FIG. 4.
Figure 4:
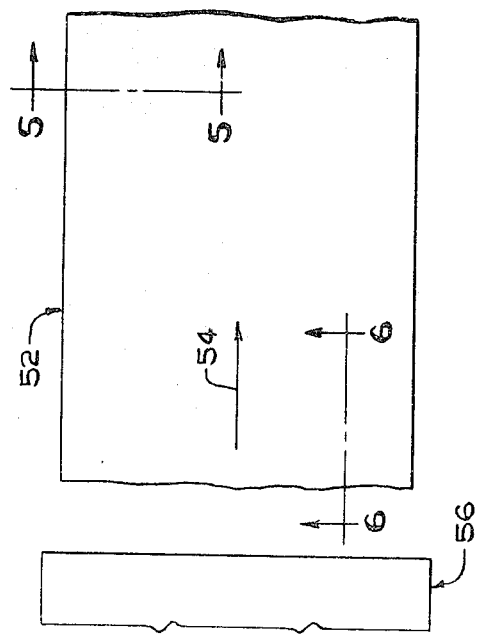
FIG. 4 is a plan view of a ribbon of interlayer material moving downstream of an extruding apparatus.

In FIG. 4, there is shown a plasticized polyvinyl acetal ribbon 52 moving in the direction of the arrow 54 downstream of a forming machine 56 of the type used in the art. For clarity of the following discussion, the movement of the ribbon in the direction of the arrow 54 is referred to as the direction of draw. In FIG. 5, there is shown a cross-section of the vinyl ribbon 52 which is transverse to the direction of draw, i.e., a cross-section of the ribbon across the draw. In FIG. 6, there is shown a cross-sectional view of the ribbon taken along a line generally parallel to the direction of draw. In FIGS. 5 and 6, thickness variations in the ribbon as shown by the cross-section of the ribbon result from peaks and valleys on each surface. The optical characteristics of a ribbon or sheet of interlayer material or ribbon is found from the thickness profile which consists of thickness variations which can be, for purposes of the discussion, considered to be the summation of the peaks and valleys of both surfaces and having the sinusoidal waves of different discrete frequencies.

During the laminating process e.g. laminating two glass sheets or one glass sheet to an interlayer material or layer material, the optical characteristics of the interlayer material change due to the temperature, hold time, and pressure variables of the laminating process. Further, the optical contribution of the internal surface of each glass sheet, are considered to be negligible because they are wetted out by the interlayer material, e.g. the interlayer material comes into contact with the glass. Therefore, the optical characteristics of the laminated product can be considered for the following discussion, but not limiting to the invention, to be a combination of the optical power contribution of the outer surface of each transparent sheet e.g. glass sheet, the internal optical power contribution of each glass sheet and the optical power contribution of the interlayer material. The optical power contribution of the interlayer material is the sum of the internal optical power contribution of the material and the thickness variations of the surfaces of the material that are not laminated or pressed out during the lamination process. Also during the laminating process, optical characteristics of the interlayer material change. For example, it has been found that thickness variations of higher frequencies, e.g. above about 2 Hertz or shorter lens width e.g. below about ½ inch (1.27 centimeter) are attenuated more than lower frequencies, e.g. below about ¼ Hertz or longer lens width e.g. above about 2 inches (5.08 centimeter). Therefore in accordance to the teachings of the invention the optical power of the interlayer material and/or expected optical power of the interlayer material in the laminated produce can be determined by simulating the lamination process by the use of filters.

Although not limiting to the invention the selection of the filter value preferably (1) simulates the removal or altering of frequencies expected to be laminated out and (2) are below those frequencies at which the optical contribution of the glass sheets is significant. In regard to the latter, it has been found that optical power contributions of glass below frequencies of about 1.1 and preferably below about 0.75 Hertz are minimal as shown by the graphs of FIGS. 7-10 showing optical power signal as passing through a 0.75 Hertz filter. FIG. 7 shown as optical power signal of a first piece of commercial float glass about 0.070 inches (0.18 centimeters) thick, taken along a scan path across the draw of the glass; FIG. 9 shows an optical power signal of the same piece of glass taken along a scan path with the draw; FIG. 8 shows an optical power signal of a second piece of commercial float glass about 0.070 inches (0.18 centimeters) thick taken along a scan path across the glass draw and FIG. 10 shows the optical power signal of the second piece of glass taken along the scan path with the draw. As can be observed from the graphs of FIGS. 7-10, (1) at low frequencies, e.g., below 0.75 Hertz the optical power value of the glass is small indicating minimal optical power contribution by the glass and (2) for the same frequencies, the optical power contribution of the glass is smaller with the draw than across the draw. As can now be appreciated, the optical power value of a laminate is predominantly the optical power contribution of the interlayer material when the laminate is made of two glass sheets about interlayer material and the laminate is scanned at a frequency at or below 0.75 Hertz along a scan path with the draw of the glass.

Figure 11:
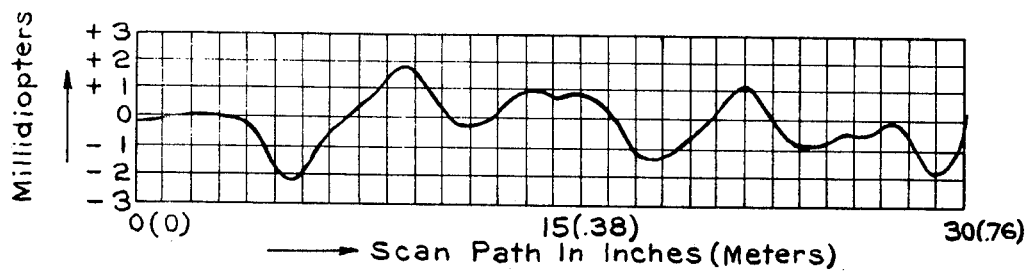
FIG. 11 is optical power signal of a sheet of interlayer material taken along a scan path across the draw.
Figure 12:
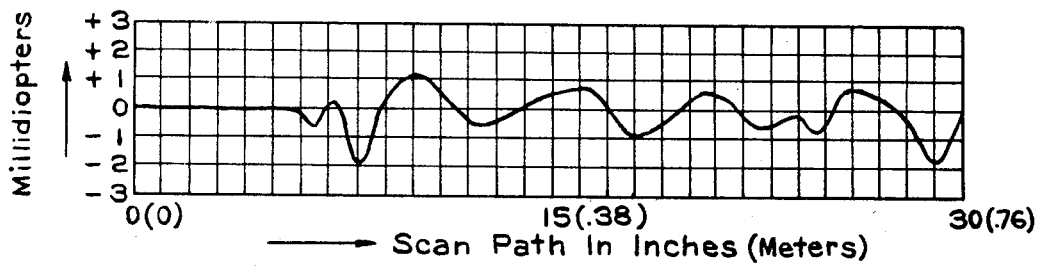
FIG. 12 is optical power signal of a laminate made with glass sheets of FIGS. 7 and 8 and interlayer material of FIG. 11 taken along a scan path with the draw of the interlayer and with the draw of the glass sheets.

FIG. 11 shows optical power signal below frequencies of 0.5 Hertz of an interlayer material taken along a scan path across the draw and FIG. 12 shows optical power signal below frequencies of 1.1 Hertz of a laminate taken along a scan path across the draw of the interlayer material and with the draw of the glass. The optical power signal of the glass sheets used in the laminate at frequencies below 0.75 Hertz are shown in FIGS. 9 and 10. A study of FIGS. 9-12 clearly shows that the optical power signal of the interlayer material below frequencies of about 0.5 Hertz can be used to predict the optical power contribution of the interlayer material in the laminate.

Figure 13:
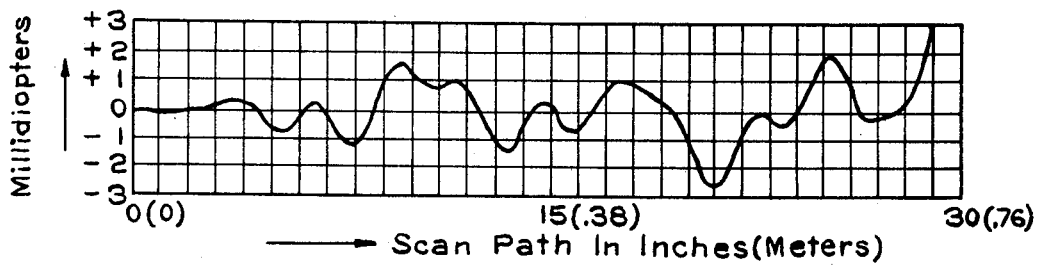
FIG. 13 is optical power signal of the sheet of interlayer material of FIG. 11 taken along a scan path with the draw.
Figure 14:
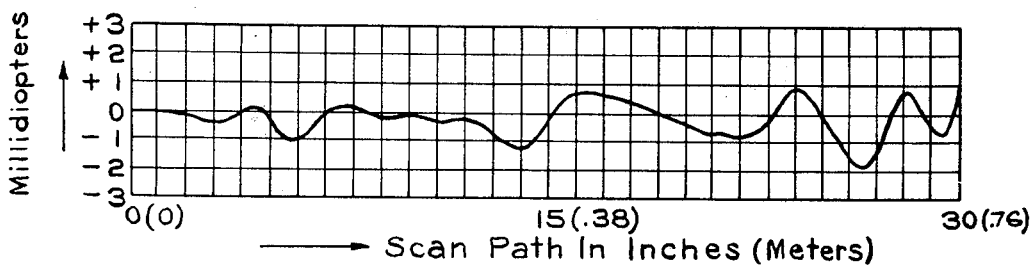
FIG. 14 is optical power signal of the laminate of FIG. 12 taken across the draw of the interlayer.

FIG. 13 shows an optical power signal below frequencies of 0.5 Hertz of an interlayer material taken along a scan path with the draw of the interlayer material and FIG. 14 shows optical power signal below frequencies of 0.65 Hertz of a laminate taken along a scan path with the draw of the interlayer material and across the draw of the glass. The optical power signal of the glass sheets used in the laminate are shown in FIGS. 7 and 8 Although an exact prediction of the optical performance of the interlayer material in the laminate cannot be made from the optical power of the interlayer material, a similarity does exist. It is believed that the differences in the optical characteristics as shown in FIGS. 13 and 14 are caused by thickness variations of the interlayer material below certain wavelengths of about 1½ inches (3.81 centimeters) which randomly flow and are reduced in amplitude. A change in the frequency of the filter e.g. filter 100 from 0.5 Hertz to about 0.4 Hertz would be expected to give better agreement.

The instant invention may be used to determine the optical characters as described above for interlayer material after extrusion or formation and/or after stretching for subsequent use in bent laminated windshields. The optical quality of the interlayer material can be measured after extrusion of the material and again after stretching for subsequent use in bent laminated windshields by comparing the optical values before and after the stretching to determine the effect of stretching on the material. Such a test can be used to monitor the quality of the stretching process or to determine the optical contributions imposed in the interlayer material by the stretching process. By practicing the instant invention, it is possible to evaluate incoming interlayer material and determine the expected contribution of the interlayer material to the finished laminated product. If the optical contribution is such that the ultimate product will not be optically acceptable, the offending material can be rejected for use.

As can be appreciated, the electrical system shown in FIG. 3 is not limiting to the invention but is illustrative of one embodiment that may be used. Further, the invention is not limited to the filters used. As can now be appreciated, the percent of high frequencies or wavelength attenuated depend upon the lamination process parameters, e.g., temperature, pressure and hold time. Therefore filter cutoff frequencies may be determined experimentally as follows. A section of interlayer material is scanned and the thickness variation signal acted on by filters set at an arbitrary cutoff frequency that is lower than a wavelength equivalent to the width of the thickness detector gage. At this cutoff frequency the electrical noise generated by the electronics will be eliminated while the total optical characteristics of the interlayer material will be obtained. The inspected interlayer material is laminated between a pair of glass sheets and the laminated sample optically scanned. If the waveforms of the laminated article do not match the cutoff frequencies, the filters are adjusted. The process is repeated until acceptable corelation is obtained.

DETAILED DESCRIPTION OF THE INVENTION

With specific reference to FIG. 1, the inspection head 44 is a capacitance thickness gauge of the type sold by Lyon Precision Corporation of Newton, Massachusetts, Model No. TG331S. The inspection head is connected to an electrical system 104 by cable 106. The electrical system 104 has a power supply and associated electron devices for conditioning the signal from the inspection head so that the output signal along cable 36 is a function of the thickness of the material. The capacitance detector as shown in FIG. 2 includes a top plate 108 and a bottom plate 110. The top plate capacitance detector 108 has a width of about 0.1 inch (2 millimeters) and a length of about 1.5 inches (30 millimeters) with the length of the plate 108 lying transverse to the scan path 34. This type of detector is selected because the width of the plate 108 is less than or equal to the smallest lense width formed by the peaks and valleys on the surface of the interlayer material to be inspected.

With specific reference to FIG. 3, the filters 60, 64, 78, 84, 94 and 100 are identical but set at different levels discussed below. The filters are 4-pole active Butterworth filters sold by Multimetrics Inc. of Freeport, New York. With specific reference to the electrical system 38 of FIG. 2, the signal along line 36 is forwarded to 5 Hertz filter 60 to remove noise from the signal. The output signal from the filter 60 is sent along cable 62 (1) to a 0.5 Hertz filter 64 to remove frequencies expected to be attenuated during the lamination process and noise from the signal; (2) along cable 70 to differentiator 72; and (3) along cable 66 to a 6 channel Gould recorder Model No. 260. The signal along cable 66 to the recorder is the thickness variation of the interlayer material and the signal from the filter 64 along cable 74 to the recorder 68 is the expected thickness variation of the interlayer material after laminating. The differentiator 72 differentiates the signal from the filter 60. The output signal from the differentiator 72 is forwarded along cable 76 to a 2 Hertz filter 78 and the filtered signal from the filter 78 is forwarded along cable 80 to the recorder 68 and along cable 82 to a ¾ Hertz filter 84. The signal along cable 80 having the noise removed is the wedge angle of the interlayer material. The signal from the filter 84 which is the expected wedge angle contribution of the interlayer material to the laminated product is forwarded along line 86 to the recorder 68. The signal from the filter 84 is also forwarded along line 90 to second differentiator 88. The outer signal from the differentiator 88 is forward along cable 92 to filter 94. The 1 Hertz filter 94 filters noise from the signal and the output signal is forwarded along cable 96 to the recorder 68 and along cable 98 to a ½ Hertz filter 100. The signal along cable 96 is the optical power of the interlayer material. The signal forwarded from the filter 100 along cable 102 to the recorder 68 is the expected optical contribution of the interlayer material to the laminated product.

The electrical system 38 is calibrated as previously discussed by imposing a calibration thickness signal on cable 36. The calibration thickness signal shown in equation 1 has $C_1$ A = 0.001 inch (0.00254 centimeter)
s = 2 inches per second (5.08 centimeter per second)
f = 0.5 Hertz
x = 2 inches (5.08 centimeter)
B = 0

B is set to 0 because it does not contribute to the optical measurement. The calculated maximum value of wedge angle occurs when Cosine $2\pi fx/s$ of Equation 3 equals 1. With $C_2$ of Equation 3 equal to 0.0029 radians per volt Equation 3 equals 0.00157 radians which is equal to an output voltage for the differentiator 72 of about 541 millivolts.

The calculated maximum value of optical power from Equation 5 occurs when $-\sin 2\pi fx/s$ equals 1. With $C_3$ of Equation 5 set equal to 0.1 diopters per volt the optical power equals 0.051 diopters which is equal to an output voltage for the differentiator 88 of about 0.51 volts.

The leading edge of a 2½ feet (0.75 meter) square section of plasticized polyvinyl acetal sheet material is positioned between wheels 46 and 48 of the drive arrangement 42 with a portion of the interlayer material under the inspection head 44. The drive arrangement is energized to meter the sheet at a speed of about 2 inches per second 5.08 centimeters per second to scan the material along the scan path 34. A scan is made across the draw and thereafter with the draw.

Figure 15:
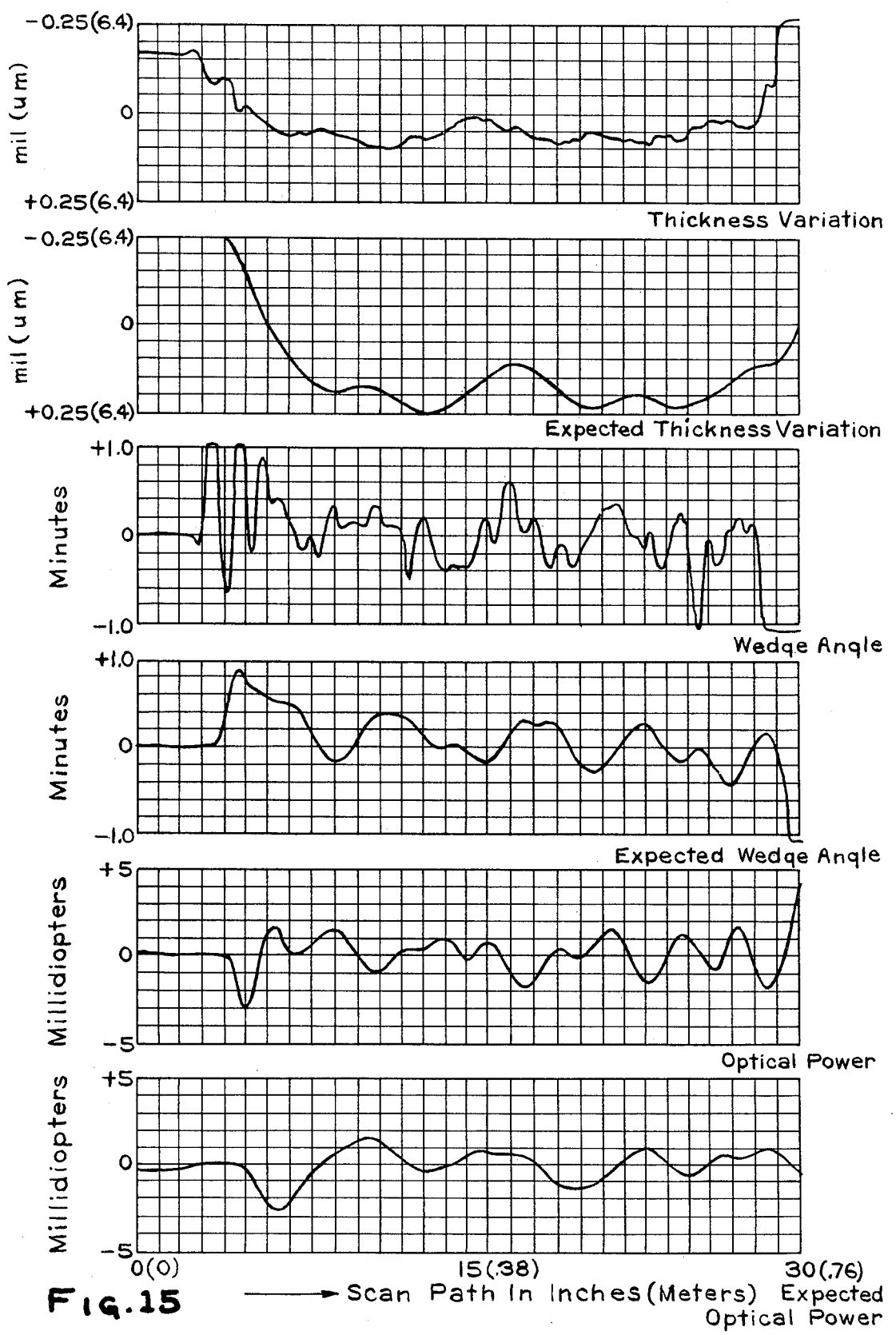
FIG. 15 is a typical chart showing thickness profile, wedge angle profile and optical power profile of an interlayer material and corresponding expected profiles of the material in the laminate taken along a scan path across the draw in accordance to the teachings of the invention.
Figure 16:
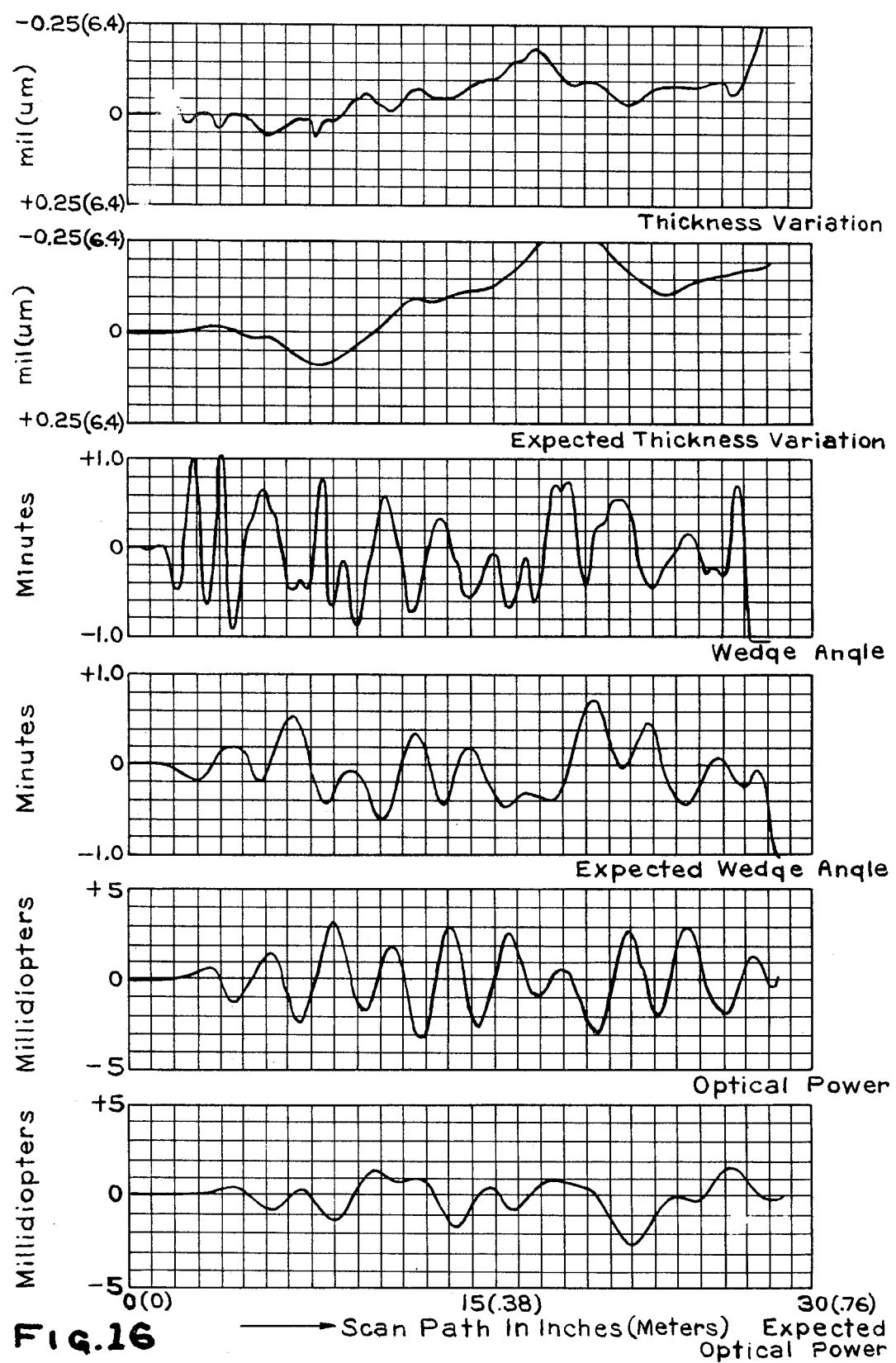
FIG. 16 is a chart similar to that of FIG. 15 of the interlayer material taken along a scan with the draw.

FIG. 15 is a typical recording chart from the recorder 68 of interlayer material scanned across the draw and FIG. 16 is a typical recording chart from the recorder 68 of the interlayer material scanned with the draw. The first graph of FIGS. 15 and 16 i.e. the topmost graph as viewed in FIGS. 15 and 16 is the output signal from the filter 60 which is the thickness variation of the interlayer material. The second graph of FIGS. 15 and 16 is the output signal from the filter 64 which is the expected thickness variation of the interlayer material in the laminate. The third graph of FIGS. 15 and 16 is the output signal from the filter 78 which is the wedge angle of the interlayer material. The fourth graph of FIGS. 15 and 16 is the output signal from the filter 84 which is the expected wedge angle contribution of the interlayer material to the laminate. The fifth graph of FIGS. 15 and 16 is the output signal from the filter 94 and is the optical power of the interlayer material. The sixth graph of FIGS. 15 and 16 is the output signal from the filter 100 and is the expected optical power contribution of the interlayer material to the laminate.

As can now be appreciated, the invention is not limited to the above example which was presented for illustration purposes only.

What is claimed is:

1. A method of determining optical property of a transparent plastic sheet defined as a worked sheet exposed to heat or pressure from a transparent plastic sheet defined as an unworked sheet prior to exposure to the heat or pressure, comprising the steps of:
   scanning the unworked sheet to generate an optical profile of the unworked sheet; and
   altering portions of the optical profile of the unworked sheet to provide an altered optical profile which is the expected optical profile of the worked sheet.

2. The method as set forth in claim 1 wherein said generating step includes the step of generating a thickness profile of the unworked sheet.

3. The method as set forth in claim 2 wherein said generating step includes the steps of:
   generating a thickness variation frequency signal; and
   said altering step includes the step of filtering frequencies above a predetermined value from the thickness variation frequency signal.

4. The method as set forth in claim 1 or 2 wherein said generating step include the step of generating a wedge angle profile of the unworked sheet.

5. The method as set forth in claim 4 wherein said generating step includes the steps of:
   generating a wedge angle frequency signal; and
   said altering step includes the step of filtering frequencies above a predetermined value from the wedge angle frequency signal.

6. The method as set forth in claim 1 wherein said generating step includes the step of generating an optical power profile of the unworked sheet.

7. The method as set forth in claim 6 wherein said generating step includes the steps of:
   generating an optical power frequency signal; and
   said altering step includes the step of filtering frequencies above a predetermined value from the optical power frequency signal.

8. The method as set forth in claim 1 wherein said step of generating an optical profile includes the steps of:
   generating a thickness variation signal of the unworked sheet;
   differentiating the thickness variation signal to provide a wedge angle signal;
   differentiating the wedge angle signal to provide an optical power signal; and
   said altering step includes the step of filtering frequencies above a predetermined value from the optical power signal.

9. An electrical system for determining optical property of a transparent plastic sheet defined as a worked sheet exposed to heat or pressure from a transparent plastic sheet defined as an unworked sheet prior to exposure to the heat or pressure, comprising:
   means for scanning the unworked sheet to generate optical profile of the unworked sheet; and
   means operatively connected to said scanning means for altering portions of the optical profile to provide an altered optical profile which is the expected optical profile of the worked sheet.

10. The system as set forth in claim 9 wherein said scanning means includes:
    means for generating a thickness variation signal of the unworked sheet; and
    said altering means includes means for attenuating the thickness variation signal.

11. The system as set forth in claim 9 wherein said scanning means includes:
    means for generating a wedge angle signal of the unworked sheet; and
    said altering means includes means for attenuating the wedge angle signal.

12. The system as set forth in claim 9 wherein said scanning means includes:
    means for generating an optical power signal of the unworked sheet; and
    said altering means includes means for attenuating the optical power signal.

13. The system as set forth in claim 9 wherein the sheet is a plastic material used in manufacture of laminates.

14. The system as set forth in claim 13 wherein said scanning means includes:
    means for generating a thickness variation signal; a wedge angle signal; and an optical power signal of the unworked sheet; and
    said altering means includes means for attenuating the thickness variation signal; the wedge angle signal; or the optical power signal.

* * * * *